United States Patent [19]
Kiritoshi et al.

[11] Patent Number: 5,925,617
[45] Date of Patent: Jul. 20, 1999

[54] PROPHYLACTIC/THERAPEUTIC COMPOSITION FOR SECONDARY CATARACT

[75] Inventors: Akira Kiritoshi, Osaka; Tetsuo Sasabe, Minoo; Shigeru Kamei, Takarazuka; Yasutaka Igari, Kobe; Noriko Watanabe, Osaka, all of Japan

[73] Assignee: Senju Pharmaceutical Co., Ltd., Osaka, Japan

[21] Appl. No.: 08/807,464

[22] Filed: Feb. 27, 1997

[30] Foreign Application Priority Data

Feb. 29, 1996 [JP] Japan ................... 8-042986

[51] Int. Cl.⁶ ............... A61K 38/00; C07K 5/00; C07K 7/00; C07K 17/00
[52] U.S. Cl. ............... 514/11; 514/9; 514/18; 530/317; 530/330; 530/331
[58] Field of Search ................... 530/317, 330, 530/324; 514/18, 12

[56] References Cited

U.S. PATENT DOCUMENTS 4,792,525 12/1988 Ruoslahti et al. ............... 530/330
5,629,294 5/1997 diZerega et al. ............... 530/330

OTHER PUBLICATIONS

T. Sasabe et al., "Differential Effects of Fibronectin–Derived Oligopeptides on the Attachment of Rabbit Lens Epithelial Cells in vitro", Ophthalmic Research, 1996, 28, pp. 201–208.

*Primary Examiner*—Cecilia J. Tsang
*Assistant Examiner*—S. G. Marshall
*Attorney, Agent, or Firm*—Wenderoth, Lind & Ponack, LLP

[57] ABSTRACT

The present invention is to provide a prophylactic/therapeutic composition for the secondary cataract comprising a polypeptide having an inhibitory activity of cell adhesion and a lactic acid-glycolic acid polymer.

The composition of the present invention inhibits adhesion and extension of lens epithelial cells onto the posterior lens capsule after extraction of lens and is useful as a prophylactic/therapeutic composition for the secondary cataract in the clinical point of view.

13 Claims, No Drawings

SEQUENCE LISTING (1) GENERAL INFORMATION:

(iii) NUMBER OF SEQUENCES:  4

(2) INFORMATION FOR SEQ ID NO:1:

(i) SEQUENCE CHARACTERISTICS:
      (A) LENGTH:  4 amino acids
      (B) TYPE:  amino acid
      (C) STRANDEDNESS:  single
      (D) TOPOLOGY:  linear (ii) MOLECULE TYPE: peptide (xi) SEQUENCE DESCRIPTION: SEQ ID NO:1:

-continued

```
Arg Gly Asp Ser
1

(2) INFORMATION FOR SEQ ID NO:2:

(i) SEQUENCE CHARACTERISTICS:
        (A) LENGTH:  3 amino acids
        (B) TYPE:   amino acid
        (C) STRANDEDNESS:  single
        (D) TOPOLOGY:  linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note= "Xaa at position 2 is MeGly"

(xi) SEQUENCE DESCRIPTION: SEQ ID NO:2:

Arg Xaa Asp
1

(2) INFORMATION FOR SEQ ID NO:3:

(i) SEQUENCE CHARACTERISTICS:
        (A) LENGTH:  5 amino acids
        (B) TYPE:   amino acid
        (C) STRANDEDNESS:  single
        (D) TOPOLOGY:  linear (ii) MOLECULE TYPE: peptide (xi) SEQUENCE DESCRIPTION: SEQ ID NO:3:

Tyr Ile Gly Ser Arg
1               5

(2) INFORMATION FOR SEQ ID NO:4:

(i) SEQUENCE CHARACTERISTICS:
        (A) LENGTH: 4 amino acids
        (B) TYPE:   amino acid
        (C) STRANDEDNESS:  single
        (D) TOPOLOGY:  linear (ii) MOLECULE TYPE: peptide (ix) FEATURE:
        (A) NAME/KEY:
        (B) LOCATION:
        (C) IDENTIFICATION METHOD:
        (D) OTHER INFORMATION: /note= "Xaa at position 2 is MeGly; Xaa
            at position 4 is other; peptide is cyclic"

(xi) SEQUENCE DESCRIPTION: SEQ ID NO:4:

Arg Xaa Asp Xaa
```

PROPHYLACTIC/THERAPEUTIC COMPOSITION FOR SECONDARY CATARACT

BACKGROUND OF THE INVENTION

1. Field of the Invention

The present invention relates to a prophylactic/therapeutic composition for the secondary cataract.

2. Description of Related Art

Since implantation of an intraocular lens was accepted widely in the operation of cataract, fixation of the intraocular lens in the bag has been considered to be the best method in physiological aspect and various operation techniques have been worked out. Among them, a method of the highest authenticity is an envelope technique which incises a part of the anterior capsule, removes the lens cortex and nucleus with aspirating and inserts the intraocular lens from the incised part. In this method, however, the aftercataract, namely the secondary cataract of which opacification of the posterior capsule results from migration and proliferation of the residual lens epithelial cells onto the posterior lens capsule occurs frequently. A physical therapy such as Laser Nd:YAG capsulotomy method, etc. is generally used for treatment of the secondary cataract. However, a risk of causing degeneration of the intraocular lens is pointed out and, therefore, a prophylaxis/therapy for the secondary cataract by medication after implantation of the intraocular lens has been long-awaited.

For the prophylaxis/therapy for the secondary cataract by medication, Arg-Gly-Asp (hereinafter referred to as "RGD", sometimes), a peptide as a minimum unit which is essential to binding between fibronectin and a receptor thereof or an oligomer thereof has been studied. However, it is still insufficient for clinical application as drugs [Atarashii Ganka (Journal of the Eye) Vol. 10, (7): 1235–1238 (1993)].

It is known that Arg-Gly-Asp (RGD) or a compound having an affinous sequence inhibits binding between not only fibronectin but also the other cell adhesive factor and the receptor. Japanese Patent Unexamined Publication No. 316193/1995 discloses a method of synthesizing a cyclic peptide derivative represented by cyclo(-Arg-MeGly-Asp-R)b (SEQ ID NO. 4) ('b' represents an integer of not less than 1) as the above compound or use thereof, R represents an amino acid residue or peptide residue, and Japanese Patent Unexamined Publication No. 3190/1996 (U.S. Pat. No. 5,183,804) discloses a method of synthesizing a polypeptide represented by (Tyr-Ile-Gly-Ser-Arg)c (SEQ ID NO:3) ('c' represents an integer of 1 to 20) as the above compound or use thereof, but use for the secondary cataract is not known yet.

SUMMARY OF THE INVENTION

It is an object of this invention to provide a practical prophylactic/therapeutic composition for the secondary cataract.

Through intensive research, the present inventors have found a polypeptide-sustained release preparation having an inhibitory activity of cell adhesion is unexpectedly useful for preventing or treating the secondary cataract. Based upon the above finding, the present invention has been accomplished.

That is the present invention is to provide:

(1) a prophylactic/therapeutic composition for the secondary cataract comprising a polypeptide having an inhibitory activity of cell adhesion and a lactic acid glycolic acid polymer;

(2) the composition according to (1), wherein a molar ratio (%) of lactic acid to glycolic acid of the lactic acid-glycolic acid polymer is from about 100:0 to 40:60;

(3) the composition according to (1), wherein a weight average molecular weight of the lactic acid-glycolic acid polymer is from about 3,000 to 50,000;

(4) the composition according to (1), wherein the polypeptide is a chain or cyclic polypeptide having a molecular weight of not more than 10,000 and having an amino acid sequence of Arg-Gly-Asp-Ser, Arg-MeGly-Asp or Tyr-Ile-Gly-Ser-Arg in the structure thereof;

(5) the composition according to (1), which is in a form of microcapsule;

(6) the composition according to (1), which is used for intraocular injection; and (7) the composition according to (1), which is used for insertion of an intraocular lens.

(8) Use of the composition according to (1) for preventing/treating the seconday cataract.

DETAILED DESCRIPTION OF THE INVENTION

Abbreviations for amino acids, peptides and protective groups used in the present specification are based on the abbreviations specified by the IUPAC-IUB Communication on Biochemical Nomenclature or abbreviations in common use in the relevant fields. When an optical isomer may be present in amino acid, it is of the L-configuration, unless otherwise stated.

The polypeptide used in the present invention is not specifically limited, so far as it has an inhibitory activity of cell adhesion. For example, there can be used a chain or cyclic polypeptide having an amino acid sequence of Arg-Gly-Asp-Ser (SEQ ID NO. 1), Arg-MeGly-Asp (SEQ ID NO. 2) or Tyr-Ile-Gly-Ser-Arg (SEQ ID NO. 3) in the structure thereof, such as 1. a polypeptide represented by the formula:

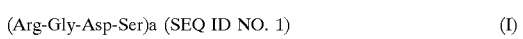

(Arg-Gly-Asp-Ser)a (SEQ ID NO. 1)    (I)

[wherein 'a' represents an integer of not less than 1] or a salt thereof;

2. a cyclic polypeptide represented by the formula:

cyclo(-Arg-MeGly-Asp-R-)b (SEQ ID NO. 4)    (II)

[wherein MeGly represents an α-N-methylglycine residue, R represents an amino acid residue or a peptide residue, and 'b' represents an integer of not less than 1] of a salt thereof; and 3. a polypeptide represented by the formula:

(Tyr-Ile-Gly-Ser-Arg)c (SEQ ID NO. 3)    (III)

[wherein 'c' represents an integer of 2 to 20] or a salt thereof.

In the compound (I), 'a' is an integer of not less than 1, preferably from 1 to 20.

The compound (I) has a structure wherein peptide residues in the parentheses are repeated 'a' times, but may have a cyclic structure by forming a peptide bond at both terminal ends of a chain structure or at any position in the chain structure.

In the compound (II), 'b' is an integer of not less than 1, preferably from 2 to 5 more preferably from 2 to 3. R is an amino acid residue or a peptide residue. When R is the peptide residue, the number of the amino acid residues in the peptide residue is not more than 5, preferably not more than 3. The 'Amino acid' in 'the amino acid residue' means not only α-amino acid but also other amino acids (e.g. β-amino acid, γ-amino acid, etc.). As amino acid other than α-amino acid, amino acid represented by $H_2N(CH_2)_nCOOH$ (n represents an integer of not less than 2) is preferred and examples thereof include 3-aminopropionic acid, 4-aminobutanoic acid, 5-aminopentanoic acid, 6-aminocaproic acid, 7-aminopentanoic acid, 8-aminocaprylic acid and the like. 'n' is preferably an integer of not less than 8. The α-amino acid may be any one of L-amino acid, D-amino acid and D,L-amino acid. The α-amino acid is preferably L-amino acid. Specific examples of the amino acid residue include residues of amino acid, such as phenylglycine, serine, tryptophan, valine, aspartic acid, alanine, isoleucine, phenylalanine, lysine, leucine, threonine and the like. R is preferably an amino acid residue, and a phenylglycine residue is particularly preferred.

The compound (II) has a cyclic structure wherein a peptide bond is formed at both terminal ends of a chain structure, wherein peptide residues in the parentheses are repeated 'b' times, or at any position in the chain structure.

In the compound (III), 'c' is an integer of from 1 to 20, preferably from 2 to 20. The compound (III) has a structure wherein peptide residues in the parentheses are repeated 'c' times, but may have a cyclic structure by forming a peptide bond at both terminal ends of a chain structure or at any position in the chain structure.

In the present invention, there can be preferably used the compound (I), more preferably (Arg-Gly-Asp-Ser)tetramer wherein 'a' is 4 [hereinafter referred merely to as a "RGDS tetramer", sometimes], as the polypeptide having an inhibitory activity of cell adhesion.

The above compounds (I), (II) and (III) may be used as they are, or be salts or derivatives thereof. Specific examples of the salt include salts with acids such as organic acid (e.g. acetic acid, tartaric acid, citric acid, etc.) and inorganic acid (e.g. carbonic acid, hydrochloric acid, sulfuric acid, nitric acid, phosphoric acid, etc.) and salts with bases such as organic base (e.g. organic amines such as triethylamine, etc.) and inorganic base (e.g. alkali metal such as sodium, potassium, etc. and alkaline earth metal such as calcium, magnesium, zinc, etc.).

In the present invention, the polypeptide having sufficiently high inhibitory activity of cell adhesion and high water-solubility, and a molecular weight of about 15,000 or less, preferably about 10,000 or less, are used.

The compounds (I), (II) and (III) or salts thereof can be produced by a per se known method. Specifically, they can be produced by the method described in the above [Atarashii Ganka (Journal of the Eye) Vol. 10 (7): 1235–1238 (1993)], Japanese Patent Unexamined Publication No. 316193/1995 and No. 3190/1996 or a modification thereof.

As the prophylactic/therapeutic composition for the secondary cataract of the present invention, a sustained release preparation comprising the above polypeptide and lactic acid-glycolic acid polymer (hereinafter referred to as a "polymer", sometimes) is preferred.

The lactic acid-glycolic acid polymer used in the present invention is not specifically limited, so long as it is a biodegradable polymer substance, but a polymer synthesized by dehydrating polycondensation in the absence of a catalyst is preferred. Examples of the method of producing the lactic acid-glycolic acid polymer according to dehydrating polycondensation in the absence of a catalyst include the production method described in Japanese Patent Unexamined Publication No. 26521/1986 (EP 0171907) and the like.

The lactic acid-glycolic acid polymer used in this invention includes a homopolymer of lactic acid and a copolymer of lactic acid and glycolic acid. The polymerization of the lactic acid-glycolic acid copolymer may be random, block or graft polymerization. When lactic acid and glycolic acid have an optically active center in the molecule, all of D-, L- and DL-configuration can be used.

The molar ratio (%) of lactic acid to glycolic acid in the lactic acid-glycolic acid polymer is generally aboudt 100:0 to 40:60, preferably about 99:1 to 40:60, more preferably about 90:10 to 50:50.

The weight-average molecular weight of the lactic acid-glycolic acid polymer is preferably from about 3,000 to 5,000, more preferably from about 5,000 to 20,000. The dispersity (weight-average molecular weight/number average molecular weight) of the lactic acid-glycolic acid polymer is preferably from about 1.2 to 4.0, more preferably from about 1.5 to 3.5.

In the present invention, there can be used biodegradable polymer substances such as polymer synthesized from one of α-hydroxycarboxylic acids (e.g. glycolic acid, lactic acid, etc.) by dehydrating polycondensation in the absence of a catalyst, polymer or copolymer synthesized from one of hydroxydicarboxylic acids (e.g. maleic acid), hydroxytricarboxylic acids (e.g. citric acid, etc.) by dehydrating polycondensation in the absence of a catalyst or a mixture thereof, poly-α-cyanoacrylate, polyamino acid (e.g. poly-γ-benzyl-L-gulutamic acid etc.) and maleic anhydride polymer (e.g. styrene-maleic acid polymer, etc.), in addition to the lactic acid-glycolic acid polymer. The polymerization of the biodegradable polymer substance may be random, block or graft polymerization. When the above α-hydroxycarboxylic acids, hydroxydicarboxylic acids and hydroxytricarboxylic acids have an optically active center in the molecule, all of D-, L- and DL-configuration can be used.

As the biodegradable polymer substance used in the present invention, there can be further used protein (e.g. gelatin, collagen, elastin, fibrin, etc.), polysaccharides (e.g. hyaluronic acid, dextran, alginic acid, pullulan, pectin, amylopectin, ether cellulose, etc.) and the like.

It may also be used a biocompatible polymer substance (e.g. methyl methacrylate polymer, 2-hydroxyethyl methacrylate polymer, 6-nylon, polypropylene, poyvinylidene fluoride, polysulfone, ethylene-vinyl acetate, polyimide, etc.), which is a main constituent polymer of the intraocular lens, in combination with the above lactic acid-glycolic acid polymer or other biodegradable polymer substances.

The above-mentioned biodegradable polymer substances or biocompatible polymer substances can be used in any amount so long as they do not hamper the sustained release property of the preparation and inhibitory activity of the drug on cell adhesion, and it is preferable to use them in an amount not to exceed a half weight part relative to the total amount of the polymer substances used.

The weight-average molecular weight, number-average molecular weight and dispersity in the present specification respectively mean a molecular weight in terms of polystyrene measured by gel permeation chromatography (GPC) using nine kinds of polystyrenes having a weight-average molecular weight of 120,000 52,000, 22,000, 9,200, 5,050, 2,950, 1,050, 580 and 162 as a reference substance, and a calculated dispersity. The measurement was conducted by using a GPC column KF804Lx2 (manufactured by Showa Denko Co., Ltd.) and a RI monitor L-3300 (manufactured by Hitachi Ltd.) and using chloroform as a mobile phase.

Examples of the method of producing the sustained release preparation include the following methods.

I. Method for producing microcapsule from polymer which is soluble in organic solvent (A) In-water drying method In this method, a W/O type emulsion wherein an aqueous solution of a polypeptide having an inhibitory activity of cell adhesion or a salt thereof (hereinafter referred merely to as "drug", sometimes) is emulsified in an organic solvent solution of a polymer or a S/O type emulsion wherein a drug is dispersed in an organic solvent solution of a polymer is firstly prepared (hereinafter, these W/O type emulsion and S/O type emulsion are sometimes referred to as an "oil phase containing a drug"). In this case, a concentration of the polymer in the organic solvent solution varies depending on the kind of the polymer and molecular weight and kind of the organic solvent, and is preferably from about 0.01 to 90% (w/w), more preferably from about 0.1 to 80% (w/w), particularly from about 1 to 70% (w/w).

It is preferred that the above organic solvent has a boiling point of not higher than 120° C. Examples of the organic solvent include halogenated hydrocarbons (e.g. dichloromethane, chloroform, carbon tetrachloride, etc.), alcohols (e.g. ethanol, methanol, etc.), acetonitrile, acetone and the like. These may be used in combination in an appropriate proportion. The organic solvent is preferably dichloromethane, acetonitrile or acetone. Among them, dichloromethane and acetone are particularly preferred.

When the aqueous solution of the drug is emulsified in the organic solvent solution of the polymer, a concentration of the drug in the aqueous solution varies depending on the kind, molecular weight or solubility in water of the drug used. For example, the concentration of the drug is from about 0.001 to 200% (w/v), preferably from about 0.001 to 100% (w/v), more preferably from about 0.01 to 80% (w/v), particularly from about 0.05 to 70% w/v). In this case, pH adjustors, stabilizers and preservatives may be added to the aqueous solution.

A volume ratio of the aqueous solution of the drug to the organic solvent solution of the polymer is from about 1:1,000 to 1:1, more preferably from about 1:100 to 1:2, particularly from about 1:50 to 1:3.

In such way, the W/O type emulsion wherein the aqueous solution of the drug is emulsified in the organic solvent solution of the polymer is produced.

When the drug is dispersed in the organic solvent solution of the polymer, a concentration of the polymer in the organic solvent solution is the same as that described above. A weight ratio of the drug to the polymer is from about 1:1,000 to 1:1, more preferably from about 1:200 to 1:2, particularly from about 1:100 to 1:5.

The above emulsification and dispersion can be conducted, for example, by a known method using a turbine stirrer, a homogenizer and the like.

A microcapsule is prepared by adding the oil phase containing the drug thus prepared to an aqueous phase containing an emulsifier (e.g. anionic surfactant, nonionic surfactant, polyoxyethylene castor oil derivative, polyvinyl pyrrolidone, polyvinyl alcohol, carboxymethylcellulose, lecithin, gelatin, hyaluronic acid, etc.) to form a W/O/W type or S/O/W type emulsion, and then removing the solvent in the oil phase according to a known method for removing the solvent (e.g. method of evaporating the solvent with stirring using a marine propeller type stirrer or a magnetic stirrer under normal pressure or gradually reduced pressure, method of evaporating the solvent with a rotary evaporator, etc. under controlling a vacuum pressure).

The emulsifiers may be used singly or in combination, and a concentration of the emulsifier in the aqueous phase can be appropriately selected from the range of about 0.001 to 20% (w/w), more preferably from about 0.01 to 10% (w/w) a particularly from about 0.05 to 5% (w/w).

The microcapsule thus prepared is collected by centrifugation or filtration. After the emulsifier adhered to the surface of the microcapsule is removed repeatedly by washing with water, the microcapsule is dispersed again in water and then freeze-dried. If necessary, the microcapsule is heated under reduced pressure to remove water and the organic solvent from the microcapsule. This operation is preferably conducted at a temperature several degree higher than the intermediate glass transition temperature of the polymer determined by a differential scanning calorimeter under controlling of elevation of the temperature at 10–20° C./minute, more preferebly at a temperature ranging from an intermediate glass transition tempereture of the polymer to 30° C. higher, furthermore preferably to 20° C. higher, particularly to 10° C. higher than the intermediate glass transition temperature of the polymer, within one week or 2 or 3 days, more preferably within 12–24 hours after the microcapsule itself is heated at the predetermined temperature.

(B) Phase separation method

When the microcapsule is produced by this method, a coacervating agent is gradually added to the oil phase containing the drug of the above method (A) with stirring to deposit a polymer which is then solidified. An amount of the coacervating agent is selected from about 0.01- to 1000-fold, more preferably from about 0.05- to 500-fold, particularly from about 0.1- to 20-fold, of the volume of the oil phase.

The coacervating agent is not specifically limited, so far as it is a polymer, mineral oil or vegetable oil which is miscible with the organic solvent dissolving the polymer and not dissolving the polymer. Specifically, silicone oil, sesame oil, soybean oil, corn oil, cottonseed oil, coconut oil, linseed oil, mineral oil, n-hexane, n-heptane, etc. are used. Two or more of them may be used in combination.

If necessary, the water and organic solvent in the microcapsule are further removed by heating under reduced pressure in the same manner as that described in the above method (A).

In order to prevent aggregation of microcapsules in the production step of the in-water drying method and phase separation method, aggregation inhibitors may be added. Examples of the aggregation inhibitor include water-soluble polysaccharides such as mannitol, lactose, glucose and starches (e.g. cornstarch, etc.); protein such as glycine, fibrin, collagen, etc.; and inorganic salts such as sodium chloride, sodium hydrogen phosphate, etc.

(C) Spray-drying method

When the microcapsule is produced by this method, the oil phase containing the drug of the above method (A) is sprayed into a drying chamber of a spray drier from a nozzle, and then the organic solvent in atomized liquid drops is evaporated within a very short time to prepare a particulate microcapsule. Examples of the nozzle include two fluid nozzle, pressure nozzle, rotary disc nozzle and the like.

Regarding the microcapsule thus obtained, if necessary, the water and organic solvent in the microcapsule are further removed by heating under reduced pressure in the same manner as that described in the above method (A).

II. Method of producing sustained release preparation by the use of a polymer which is soluble in organic solvent according to spray-casting method When the sustained release preparation is produced by this method, it is prepared by a per se known method, for example, method of quickly spray-casting the oil phase containing the drug of the above method I(A) on the non-adherent surface with a device such as air brush, etc. Examples of the material of non-adherent surface include polypropylene, teflon, nylon, polyethylene or a derivative thereof and among them, polypropylene, teflon and polyethylene are preferred. A thickness of the spray-casted film can be adjusted within the range from about 5 to 1,000 μm.

III. Method for producing microcapsule from polymer which is soluble in water

An aqueous gelatin solution wherein the drug is dissolved or dispersed is dispersed in an oil phase such as soybean oil, silicone oil, etc. to form a W/O type emulsion, which is then solidified by a known method such as a method of heating the emulsion to 120–160° C. or adding a crosslinking agent to obtain a preparation.

In this case, the solidification step may be conducted after the unsolidified microcapsule was recovered and formed into a film.

The prophylactic/therapeutic composition for the secondary cataract of the present invention can be in various dosage forms by using the above sustained release preparation (e.g. microcapsule, etc.) as it is or as a raw material, and can be administered parenterally, for example, in the form of injectable, implantable or external preparations.

The prophylactic/therapeutic composition for the secondary cataract of this invention is preferably in the form of the microcapsule.

When the prophylactic/therapeutic composition for the secondary cataract is in the form of the microcapsule, fine particles are particularly preferred. A particle size of the microcapsule may be within the range where the dispersity and needle passage are satisfied when using it as a suspension injection. For example, an average particle size is within the range from about 0.1 to 300 μm, preferably from about 1 to 150 μm, more preferably from about 2 to 100 μm.

In order to obtain the above microcapsule as a sterile preparation, a method of making all producing steps sterile, a method of sterilizing with γ-ray and a method of adding a preservative are used but are not specifically limited.

The prophylactic/therapeutic composition for the secondary cataract of this invention is preferably in the form of the injection. For example, in order to prepare the injection of microcapsule obtained by the above method, the microcapsule is combined with artificial perfusates [e.g. Opegard MA (trademark), manufactured by Senju Pharmaceutical Co. Ltd.], physiological saline for injection, dispersants (e.g. surfactants such as Tween 80, HCO-60, etc., polysaccharides such as sodium carboxylmethylcellulose, sodium alginate, etc.), preservatives (e.g. methylparaben, propylparaben, etc.), isotonic agent (e.g. sodium chloride, mannitol, sorbitol, glucose, etc.) and local anesthetics (e.g. xylocaine hydrochloride, chlorobutanol, etc.) to form an aqueous suspension, or dispersed with a mixture of vegetable oils (e.g. sesame oil, corn oil, etc.) and phospholipids (e.g. lecithin, etc.) or intermediate-chain fatty acid triglyceride (e.g. Migriol 812) to form an oily suspension. The injectable preparation can be administered locally (e.g. intraocularly) intramuscularly or intravenously.

In order to produce an implantable preparation, the form of the molded material may be any form (e.g. film, ring, plug, etc.) which can be integrated with the optical or supporting part of the intraocular lens or which can be administered to or implanting in the aqueous chambers of eyes or the vicinity thereof, and is not specifically limited. Specifically, the following form can be taken using the microcapsule obtained by the above method as a starting material.

(a) A preparation having a cylindrical rod shape is produced, and one or more of them are mounted to the supporting part of the intraocular lens and simultaneously inserted into eyes.

(b) A concentric-shaped groove is made on the outer edge part of the intraocular lens without interfering with the light transmission part of the intraocular lens, followed by implanting it in the groove.

(c) A ring having a thin film shape is made, and is press-bonded on the outer edge part of the intraocular lens without interfering with the light transmission part of the intraocular lens.

(d) The supporting part of the intraocular lens is formed into a hollow pipe, followed by filling it therein. These implantable preparation can be molded by a known molding technique such as heating, compression and the like.

The dosage amount of the prophylactic/therapeutic composition for the secondary cataract varies depending on the kind and content of the drug, dosage form, duration time of drug releasing and the like, but it may be an effective amount of the polypeptide. When the prophylactic/therapeutic composition for secondary cataract is an implantable or injectable one-month type preparation, the dosage per one time of the drug, the effective ingredient can be preferably selected from the range from about 0.05 to 100 mg, more preferably from about 0.1 to 50 mg per one eye.

The dosage amount per one time of the prophylactic/therapeutic composition for the secondary cataract can be preferably selected from the range of from about 0.5 to 1,000 mg, more preferably from about 1 to 500 mg per one eye when the preparation is in a form of implantable or injectable preparation. The frequency of administration can be appropriately selected according to the kind and content of the drugs dosage form, duration time of drug releasing and the like, for example, one time per several weeks, one month or several months.

The following Examples, Reference Example and Test Examples further illustrate the present invention in detail but are not to be construed to limit the scope thereof. In the following Examples, Reference Examples and Test Examples, % is by weight unless otherwise stated.

EXAMPLE 1

A solution prepared by dissolving 200 mg of a RGDS tetramer (manufactured by Wako Pure Chemical Industries, Ltd.) in 0.3 ml of distilled water was added to a solution prepared by dissolving 1.8 g of a lactic acid-glycolic acid copolymer [lactic acid/glycolic acid molar ratio (%): 75/25, weight-average molecular weight: 14,000, dispersity: 3.4, manufactured by Wako Pure Chemical Industries, Ltd.] and 40 mg of arginine in 3.5 ml of dichloromethane, followed by mixing with a portable homogenizer for 60 seconds to obtain a W/O type emulsion. This emulsion was cooled to 18° C. and poured into 400 ml of an aqueous 5% (W/V) mannitol-containing 0.1% polyvinyl alcohol (EG-40, manufactured by Nihon Synthetic Chemical Industry Co., Ltd.) adjusted previously to 18° C., and then a W/O/W emulsion was prepared using a turbine type homomixer at 7,000 rpm. This W/O/W emulsion was stirred at room temperature for 3 hours to evaporate dichloromethane. The oily phase was solidified and then collected with a centrifugal separator (05PR-22, manufactured by Hitachi Ltd.) at 2,000 rpm. This was dispersed again in distilled water and the dispersion was centrifuged to wash off the liberated drugs. The collected microcapsule was dispersed again with a small amount of water, and then freeze-dried to obtain a powder. The rate of the RGDS tetramer encapsuled into the microcapsule was 91.5%.

TEST EXAMPLE 1

Effect of the microcapsule on extension of lens epithelial cells onto posterior lens capsule after extracting lens and implanting intraocular lens in rabbit After lenses of Japanese albino male rabbit (body weight: 2 kg) were extracted by phacoemulsification and aspiration, the microcapsule obtained in Example 1 was suspended in a saline for injection and the resulting suspension was injected into the anterior capsules at the time of inserting intraocular lens (manufactured by Nidec Co., Ltd.). One and two weeks after operation, eyes were extracted and histopathologic samples were respectively prepared according to a usual method. Then, extension and stratification of lens epithelial cells onto the posterior lens capsule were observed with an optical microscope.

As a result, extension and stratification of lens epithelial cells onto the posterior lens capsule were significantly inhibited.

REFERENCE EXAMPLE 1

Effect on the extension of lens epithelial cells after extraction of lens and implantation of intraocular lens in rabbits After lenses of Japanese albino male rabbit (body weight: 2 kg) were extracted by phacoemulsification and aspiration, a mixture of RGDS tetramer and ethylene-vinyl acetate was simultaneously implanted at the time of inserting intraocular lens (manufactured by Nidek Co., Ltd.). One and two weeks after operation, eyes were extracted and histopathologic samples were respectively prepared according to a usual method. Then, extension and stratification of lens epithelial cells onto the posterior lens capsule were observed with an optical microscope.

As a result, extension and stratification of lens epithelial cells onto the posterior lens capsule were significantly inhibited.

TEST EXAMPLE 2

After about 20 mg of the microcapsule obtained in Example 1 and 10 ml of an aqueous 0.1% polyvinyl alcohol solution warmed previously to 37° C. were added to a vial, the vial was stirred with shaking at 37° C. at 120 cycles/minute and 150 µl of the supernatant was sampled with the passage of time. The amount of the RGDS tetramer in the supernatant was determined by HPLC and the amount of the RGDS tetramer released was calculated. The results are shown in Table 1.

TABLE 1

| Time (hr) | Proportion (%) of RGDS tetramer released |
|---|---|
| 6 | 18.6 |
| 24 | 24.9 |
| 48 | 31.4 |

As is apparent from the results of Table 1, it was confirmed that a RGDS tetramer was released long-lastingly.

TEST EXAMPLE 3

Inhibitory effect of sustained release preparation on adhesion of cultured lens epithelial cells of rabbits Test drug: $(RGDS)_4$-containing microcapsule (720 µg of drug/8 mg of microcapsule)

Test method: the drug-containing microcapsule was suspended in 8 ml of Dulbecco's modified Eagle's medium (DMEM). The culture was incubated for 24 hours, and the drug was released. The supernatant of the culture medium was collected by centrifugation and the deposit was suspended in 8 ml of DMEM again. The same releasing operation of the drug was repeated every 24 hours for 10 days and the supernatant was collected. The lens epithelial cells were cultured for 24 hours in each DMEM collected as the supernatant including the released drug. After finishing the cultivation, the DMEMs were removed from the culture dish. The residual cells which adhered on the bottom of dish were stained by the method of Giemsa stain, and then the number of stained cells was counted.

Results: The number of the stained lens epithelial cells in all the collected DMEM including drug were very few compared with the control. Percent inhibition of adhesion of cultured lens epithelial cells of rabbits was more than 90% in every culture media of 1 to 10 days.

The prophylactic/therapeutic agent for secondary cataract of the present invention inhibits adhesion and extension of lens epithelial cells onto the posterior lens capsule after extraction of lens, and is useful as a prophylactic/therapeutic agent for secondary cataract in the clinical point of view.

What is claimed is:

1. A method for treating or inhibiting development of secondary cataract, comprising the steps of:

administering to a patient in need thereof an ophthalmic composition comprising an effective amount of a polypeptide having a molecular weight of not more than 10,000 (and having an amino acid sequence of Arg-Gly-Asp-Ser (SEQ ID NO. 1) in the polypeptide, and an effective amount of a lactic acid-glycolic acid polymer.

2. The method according to claim 1, wherein the lactic acid-glycolic acid polymer has a molar ratio (%) of lactic acid to glycolic acid from about 100:0 to 40:60.

3. The method according to claim 1, wherein the lactic acid-glycolic acid polymer has a weight-average molecular weight from about 3,000 to 50,000.

4. The method according to claim 1, which is administered in the form of a microcapsule.

5. The method according to claim 1, which is administered by intraocular injection.

6. The method according to claim 1, which is administered by implantation.

7. A method for treating or inhibiting development of secondary cataract, comprising administering an ophthalmic composition to a patient in need thereof, wherein the ophthalmic composition comprises an effective amount of a polypeptide which inhibits cell adhesion together with an effective amount of a lactic acid-glycolic acid polymer.

8. The method according to claim 7, wherein the polypeptide is a chain or cyclic polypeptide having a molecular weight of not more than 10,000 and having an amino acid sequence of Arg-Gly-Asp-Ser, (SEQ ID NO:1) Arg-MeGly-Asp (SEQ ID NO. 2) or Tyr-Ile-Gly-Ser-Arg (SEQ ID NO. 3) in the polypeptide.

9. The method according to claim 7, wherein the lactic acid-glycolic acid polymer has a molar ratio (%) of lactic acid to glycolic acid from about 100:0 to 40:60.

10. The method according to claim 7, wherein the lactic acid-glycolic acid polymer has a average molecular weight from about 3,000 to 50,000.

11. The method according to claim 7, which is administered in the form of a microcapsule.

12. The method according to claim 7, which is administered by intraocular injection.

13. The method according to claim 7, which is administered by implantation.

* * * * *

UNITED STATES PATENT AND TRADEMARK OFFICE
CERTIFICATE OF CORRECTION

PATENT NO. : 5,925,617
DATED : July 20, 1999
INVENTOR(S) : Akira Kiritoshi et al.

It is certified that error appears in the above-identified patent and that said Letters Patent is hereby corrected as shown below:

Title page,
Item [73], please insert the following second Assignee:
-- Yasuo Tano, Hyogo, Japan --

Signed and Sealed this

Fourteenth Day of August, 2001

Attest:

*Attesting Officer*

NICHOLAS P. GODICI
*Acting Director of the United States Patent and Trademark Office*